(12) United States Patent
Nicholas et al.

(10) Patent No.: US 10,286,388 B2
(45) Date of Patent: May 14, 2019

(54) HYDROCARBON CONVERSION USING UZM-53

(71) Applicant: UOP LLC, Des Plaines, IL (US)

(72) Inventors: Christopher P. Nicholas, Evanston, IL (US); Mark A. Miller, Niles, IL (US)

( * ) Notice: Subject to any disclaimer, the term of this patent is extended or adjusted under 35 U.S.C. 154(b) by 0 days.

(21) Appl. No.: 16/186,251

(22) Filed: Nov. 9, 2018

(65) Prior Publication Data
US 2019/0091668 A1 Mar. 28, 2019

Related U.S. Application Data (60) Division of application No. 16/029,200, filed on Jul. 6, 2018, now Pat. No. 10,150,105, which is a division of application No. 15/798,375, filed on Oct. 30, 2017, now Pat. No. 10,022,711, which is a continuation of application No. PCT/US2016/039513, filed on Jun. 27, 2016.

(60) Provisional application No. 62/186,924, filed on Jun. 30, 2015.

(51) Int. Cl.
| | |
|---|---|
| C07C 1/24 | (2006.01) |
| C07C 2/58 | (2006.01) |
| C07C 2/66 | (2006.01) |
| C07C 4/06 | (2006.01) |
| C07C 4/18 | (2006.01) |
| C07C 5/03 | (2006.01) |
| C07C 6/12 | (2006.01) |
| C07C 7/11 | (2006.01) |
| C10G 45/12 | (2006.01) |
| C10G 45/34 | (2006.01) |
| C10G 45/54 | (2006.01) |
| C10G 45/64 | (2006.01) |
| C10G 47/16 | (2006.01) |
| B01J 29/70 | (2006.01) |
| C01B 39/48 | (2006.01) |
| C01B 39/12 | (2006.01) |
| C01B 39/06 | (2006.01) |
| B01J 37/08 | (2006.01) |
| B01J 37/00 | (2006.01) |
| B01J 37/04 | (2006.01) |
| B01J 37/10 | (2006.01) |
| C01B 39/46 | (2006.01) |
| C10G 25/03 | (2006.01) |
| C07C 2/12 | (2006.01) |
| B01J 35/00 | (2006.01) |
| B01J 29/72 | (2006.01) |

(52) U.S. Cl.
CPC ......... B01J 29/7046 (2013.01); B01J 37/009 (2013.01); B01J 37/04 (2013.01); B01J 37/08 (2013.01); B01J 37/10 (2013.01); C01B 39/06 (2013.01); C01B 39/12 (2013.01); C01B 39/46 (2013.01); C01B 39/48 (2013.01); C07C 2/12 (2013.01); C10G 25/03 (2013.01); C10G 45/12 (2013.01); C10G 47/16 (2013.01); B01J 29/7292 (2013.01); B01J 35/002 (2013.01); B01J 2229/42 (2013.01); C07C 2529/70 (2013.01)

(58) Field of Classification Search
CPC .... C07C 1/24; C07C 2/58; C07C 2/66; C07C 4/06; C07C 4/18; C07C 5/03; C07C 5/222; C07C 5/322; C07C 6/12; C07C 7/11; C10G 35/065; C10G 45/12; C10G 45/34; C10G 45/54
USPC ....... 585/666, 467, 475, 481, 486, 722, 752, 585/275, 654, 640, 820; 208/111.01, 208/254 H, 213, 264, 135
See application file for complete search history.

(56) References Cited

U.S. PATENT DOCUMENTS 7,390,763 B2 * 6/2008 Zones ...................... B01J 29/70
502/64

* cited by examiner

*Primary Examiner* — Thuan D Dang

(57) ABSTRACT

A new crystalline aluminosilicate zeolite comprising a MTT framework has been synthesized that has been designated UZM-53. This zeolite is represented by the empirical formula:

$$M^+_m R_r Al_{1-x} E_x Si_y O_z$$

where M represents sodium, potassium or a combination of sodium and potassium cations, R is the organic structure directing agent or agents derived from reactants R1 and R2 where R1 is diisopropanolamine and R2 is a chelating diamine, and E is an element selected from the group consisting of gallium, iron, boron and mixtures thereof. Catalysts made from UZM-53 have utility in various hydrocarbon conversion reactions.

15 Claims, 8 Drawing Sheets

HYDROCARBON CONVERSION USING UZM-53

CROSS-REFERENCE TO RELATED APPLICATIONS

This application is a Division of copending application Ser. No. 16/029,200 filed Jul. 6, 2018, which is a Division of application Ser. No. 15/798,375 filed Oct. 30, 2017, now U.S. Pat. No. 10,022,711 which is a Continuation of International Application No. PCT/US2016/039513 filed Jun. 27, 2016 which application claims benefit of U.S. Provisional Application No. 62/186,924 filed Jun. 30, 2015, the contents of which cited applications are hereby incorporated by reference in their entirety.

BACKGROUND OF THE INVENTION

This invention relates to a new aluminosilicate zeolite comprising a MTT framework designated UZM-53 and its use as a catalyst in hydrocarbon conversion processes. This zeolite is represented by the empirical formula:

$$M^+{}_m R_r Al_{1-x} E_x Si_y O_z$$

where M represents sodium, potassium or a combination of sodium and potassium cations, R is the organic structure directing agent or agents derived from reactants R1 and R2 where R1 is diisopropanolamine and R2 is a chelating diamine, and E is an element selected from the group consisting of gallium, iron, boron and mixtures thereof. UZM-53 has utility in various hydrocarbon conversion reactions such as oligomerization.

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

As used herein, zeolites may be referred to by proper name, such as ZSM-23, or by structure type code, such as MTT. These three letter codes indicate atomic connectivity and hence pore size, shape and connectivity for the various known zeolites. The list of these codes may be found in the Atlas of Zeolite Framework Types, which is maintained by the International Zeolite Association Structure Commission at http://www.iza-structure.org/databases/. The structure type MTT has been described in the literature and is known to contain 1-dimensional 10-ring channels normal to the c axis. Zeolites are distinguished from each other on the basis of their composition, crystal structure and adsorption properties. One method commonly used in the art to distinguish zeolites is x-ray diffraction.

Several related molecular sieves have been disclosed but there are significant differences between those molecular sieves and those of the present invention. Plank, Rosinski, and Rubin describe ZSM-23, the MTT type material, in U.S. Pat. No. 4,076,842 as having a $SiO_2/Al_2O_3$ ratio of from 40-250 and preferably from 50-220. ZSM-23 is synthesized using a nitrogen-containing organic cation. Valyocsik, describing an improved method of synthesis of ZSM-23 in U.S. Pat. No. 4,490,342 describes ZSM-23 as having a $SiO_2/Al_2O_3$ ratio of from 40-5000 and preferably from 50-2000. ZSM-23 is synthesized using an organic cation of the formula $(CH_3)_3N^+$—$R_1$—$^+N(CH_3)_3$. The present invention involves a $SiO_2/Al_2O_3$ ratio of less than 60, preferably less than 50 and most preferably less than 44 and is not synthesized using an organic nitrogen-containing cation. Attempts to synthesize ZSM-23 at a $SiO_2/Al_2O_3$ ratio of less than 50 led to the formation of ZSM-35, a material of FER structure type as disclosed in U.S. Pat. No. 4,016,245.

U.S. Pat. No. 4,837,000 discloses a crystalline silicate, ISI-4, with a specific XRD pattern that is synthesized in the presence of relatively large amounts of ethylene glycol or monoethanolamine.

Parker and Bibby describe the synthesis of KZ-1 in ZEOLITES 1983, 3, 8-11 from reactant compositions comprising pyrrolidine, dimethylamine or 2-aminopropane ranging from a $SiO_2/Al_2O_3$ ratio of from 55-110 to give a product with a particular XRD pattern and typically having a BET surface area of about 160 $m^2/g$. The present invention is made at lower $Si/Al_2$ ratios than KZ-1.

Di Renzo and coworkers describe in U.S. Pat. No. 5,314,674 the synthesis of a MTT zeolite with a particular XRD pattern in the absence of any nitrogenous organic agent and in the presence of ethanol. The UZM-53 of the instant invention is synthesized in the presence of two nitrogenous organic agents and in the absence of ethanol.

Zones describes SSZ-32 in U.S. Pat. No. 5,053,373 in the as-synthesized and anhydrous state as having a characteristic XRD pattern, a $SiO_2/Al_2O_3$ ratio of from 20 to less than 40 and comprising an N-lower alkyl-N'-isopropyl-imidazolium cation such as N,N'-diisopropylimidazolium cation. As prepared, the $SiO_2/Al_2O_3$ ratio is typically from 25:1 to about 37:1 and can be increased by treating the zeolite with chelating agents or acids to extract aluminum from the zeolite lattice.

Zones and coworkers describe in U.S. Pat. No. 7,390,763 the preparation of SSZ-32X, a MTT zeolite of a certain XRD pattern and a $SiO_2/Al_2O_3$ ratio of from 20 to less than 40 and preferably from 30 to 35 and comprising, in the as-synthesized and anhydrous form, an N-lower alkyl-N'-isopropyl-imidazolium cation such as N,N'-diisopropylimidazolium cation and an alkylamine such as isobutylamine.

Burton and Zones describe a process for preparing MTT zeolites and MTT zeolite compositions in U.S. Pat. No. 7,157,075 where the MTT zeolites synthesized have a composition in the as-synthesized and anhydrous state with a $SiO_2/Al_2O_3$ ratio of greater than 15, a ratio of at least one nitrogen-containing organic compound selected from a group including N,N,N',N'-tetramethylpropanediamine to $SiO_2$ of from 0.02 to 0.10 and a ratio of alkali metal cation (or alkaline earth cation or mixtures thereof) to $SiO_2$ of from 0.015 to 0.1.

Nakagawa discloses in U.S. Pat. No. 5,707,601 processes for synthesizing MTT zeolites such as SSZ-32 utilizing small amines such as isobutylamine as the organic structure directing agent. These MTT zeolites have specific XRD patterns and compositions different from those of the instant invention.

Rouleau and coworkers describe in U.S. Pat. No. 6,475,464 an MTT zeolite and process for preparing said zeolite wherein the synthesis is carried out using at least one alkylated polymethylene α-ω diammonium derivative and seeds of a zeolitic material different from the MTT zeolite to be prepared. The present invention does not utilize a diammonium compound, nor are seeds of a framework other than MTT used to crystallize the instant zeolite.

Barri describes in GB2190910 the synthesis of a product they call ZSM-23 from the crystallization of a gel comprising diisopropanolamine and having a $SiO_2/Al_2O_3$ ratio of greater than 50 and preferably in the range from 60 to 500. The present invention involves a $SiO_2/Al_2O_3$ ratio of less than 60, preferably less than 50 and most preferably less than 44.

SUMMARY OF THE INVENTION

A new material, UZM-53, has been made comprising a MTT framework that has utility in hydrocarbon processes. The present invention relates to zeolite UZM-53, the process of making it and its use as a catalyst in hydrocarbon conversion processes. This zeolite is represented by the empirical formula:

$$M^+_m R_r Al_{1-x} E_x Si_y O_z$$

where M represents sodium, potassium or a combination of sodium and potassium exchangeable cations, "m" is the mole ratio of M to (Al+E) and varies from about 0.05 to about 1, R is the organic structure directing agent or agents derived from reactants R1 and R2 where R1 is diisopropanolamine and R2 is a chelating diamine, "r" is the mole ratio of N from the organic structure directing agent or agents to (Al+E) and has a value of from about 0.4 to about 1.5, E is an element selected from the group consisting of gallium, iron, boron and mixtures thereof, "x" is the mole fraction of E and has a value from 0 to about 1.0, "y" is the mole ratio of Si to (Al+E) and varies from greater than 12 to about 30 and "z" is the mole ratio of O to (Al+E) and has a value determined by the equation: $z=(m+r1+r2+3+4 \cdot y)/2$. The zeolite UZM-53 has a framework of MTT type. It may be present in the catalyst as unmodified zeolite UZM-53 or as UZM-53 modified zeolite. The UZM-53 containing catalyst may take one of several forms, including for example, a spherical oil-dropped catalyst or an extruded catalyst.

As stated, the present invention relates to a new aluminosilicate zeolite designated UZM-53 that comprises a MTT framework. In a particular embodiment the zeolite designated as UZM-53 is characterized in that the as synthesized material has an x-ray diffraction pattern having at least the d-spacing's and intensities set forth in Table A.

TABLE A

| 2θ | d(Å) | I/I₀ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W—M |
| 19.72 | 4.50 | S |
| 20.04 | 4.43 | W—M |
| 21.00 | 4.23 | S |
| 21.50 | 4.13 | W—M |
| 22.90 | 3.88 | VS |
| 24.10 | 3.69 | VS |
| 24.62 | 3.61 | S |

TABLE A-continued

| 2θ | d(Å) | I/I₀ % |
|---|---|---|
| 25.34 | 3.51 | M—S |
| 26.02 | 3.42 | W |
| 28.30 | 3.15 | W—M |
| 31.62 | 2.83 | W—M |
| 35.60 | 2.52 | M—S |

After the UZM-53 material was calcined, the x-ray diffraction pattern shown in Table B was observed.

TABLE B

| 2θ | d(Å) | I/I₀ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W |
| 19.72 | 4.50 | VS |
| 20.04 | 4.43 | W—M |
| 21.00 | 4.23 | S |
| 21.50 | 4.13 | W |
| 22.90 | 3.88 | S |
| 24.10 | 3.69 | S |
| 24.62 | 3.61 | M |
| 25.34 | 3.51 | M |
| 26.02 | 3.42 | M |
| 28.30 | 3.15 | W—M |
| 31.62 | 2.83 | W—M |
| 35.60 | 2.52 | M |

Another aspect of the invention is a process of making the material from a low flammability reaction mixture comprising diisopropanolamine (DIPA) and a chelating diamine. Solutions of diisopropanolamine are highly preferred.

Yet another embodiment of the invention is a hydrocarbon conversion process using the zeolite of the present invention. The process comprises contacting the hydrocarbon with the zeolite at conversion conditions to give a converted hydrocarbon product. The hydrocarbon conversion processes include oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, di sproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

DETAILED DESCRIPTION OF THE INVENTION

Applicants have prepared an aluminosilicate zeolite whose topological structure comprises an MTT framework as described in ATLAS OF ZEOLITE FRAMEWORK TYPES, which is maintained by the International Zeolite Association Structure Commission at http://www.iza-structure.org/databases/. This new zeolite has been designated as UZM-53. As will be shown in detail, UZM-53 is different from the known zeolites in a number of its characteristics and finds utility as a catalyst in hydrocarbon conversion processes.

UZM-53 is represented in the as synthesized and anhydrous basis by the empirical formula:

$$M^+_m R_r Al_{1-x} E_x Si_y O_z$$

where M represents sodium, potassium or a combination of sodium and potassium exchangeable cations, "m" is the mole ratio of M to (Al+E) and varies from about 0.05 to about 1, R is the organic structure directing agent or agents derived from reactants R1 and R2 where R1 is diisopropanolamine and R2 is a chelating diamine such as tetramethylpropanediamine, "r" is the mole ratio of N from the organic structure directing agent or agents to (Al+E) and has a value of from about 0.4 to about 1.5, E is an element selected from the group consisting of gallium, iron, boron and mixtures thereof, "x" is the mole fraction of E and has a value from 0 to about 1.0, "y" is the mole ratio of Si to (Al+E) and varies from greater than 12 to about 30 and "z" is the mole ratio of O to (Al+E) and has a value determined by the equation: $z=(m+3+4 \cdot y)/2$ and is characterized in that it has an x-ray diffraction pattern having at least the d-spacing's and intensities set forth in Table A.

TABLE A

| 2θ | d(Å) | I/I₀ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W—M |
| 19.72 | 4.50 | S |
| 20.04 | 4.43 | W—M |
| 21.00 | 4.23 | S |
| 21.50 | 4.13 | W—M |
| 22.90 | 3.88 | VS |
| 24.10 | 3.69 | VS |
| 24.62 | 3.61 | S |
| 25.34 | 3.51 | M—S |
| 26.02 | 3.42 | W |
| 28.30 | 3.15 | W—M |
| 31.62 | 2.83 | W—M |
| 35.60 | 2.52 | M—S |

In an embodiment, "m" may vary from about 0.05 to about 0.75 or may vary from about 0.1 to about 0.5. In an embodiment, "y" may be greater than 12 or greater than 15 or greater than 17 or less than 25 or less than about 22 or less than about 20. In an embodiment, when M represents a combination of sodium and potassium cations, the ratio of Na⁺/K⁺ in M⁺ is in the range 0.10 to 2, and is preferably in the range of about 0.2 to about 0.9. The ratio of Na⁺/K⁺ may be in the range from about 0.2 to about 0.75. In an embodiment, "r" has a value of from about 0.9 to about 1.4.

A chelating diamine is a di-tertiary amine of the formula (R3)(R4)N(R7)N'(R5)(R6) where R3, R4, R5 and R6 are independently selected from an alkyl group having the formula $C_nH_{2n+1}$, where n is in the range from 1 to 4, R7 is an alkyl group having the formula $C_pH_{2p}$, where p is in the range from 2 to 6 and is connected to the N and N' atoms at positions x and y of the alkyl chain where x and y are independently selected from 1 to p, and where the total number of carbon atoms in the chelating diamine is in the range from 6 to 10. In an embodiment, n is 1 for at least two of R3, R4, R5 and R6. In an embodiment, at least two of R3, R4, R5 and R6 are $CH_3$. In an embodiment, R3, R4, R5 and R6 are equivalent. In an embodiment, R3, R4, R5 and R6 are equivalent and n is 1. In an embodiment, p is in the range from 3 to 5. In an embodiment, p is 3 and x and y are 1 and 3 respectively. In an embodiment, n is 1 for at least two of R3, R4, R5 and R6, p is 3 and x and y are 1 and 3 respectively. In an embodiment, R3, R4, R5 and R6 are equivalent, n is 1, p is 3 and x and y are 1 and 3 respectively. In an embodiment, the chelating diamine is tetramethylpropanediamine.

The UZM-53 material may be made from a low flashpoint reaction mixture having a composition expressed in terms of mole ratios of the oxides of:

$$aM_2O:bMX:cR1:dR2:1-eAl_2O_3:eE_2O_3:fSiO_2:gH_2O.$$

In an embodiment, the mixture that is used to make the UZM-53 contains

20Si:1Al(OH)₃:0.67NaOH:0.67KOH:6.26DIPA: 1.266TMPDA:271H₂O where M represents sodium, potassium or a combination of sodium and potassium cations, "a" has a value from about 0.4 to about 3, MX represents a halide salt of sodium, potassium or a combination of sodium and potassium cations, "b" has a value from 0 to about 12, R1 is diisopropanolamine, "c" has a value of about 8 to about 20, R2 is a chelating diamine, "d" has a value of about 0.0 to about 2, E is an element selected from the group consisting of gallium, iron, boron and mixtures thereof, "e" has a value from 0 to about 1.0, "f" has a value from greater than 30 to about 60 and "g" has a value from about 300 to about 2000. In an embodiment, "b" may be greater than 0 or greater than 0.5 or greater than about 1 or greater than about 2 or greater than about 3 or greater than about 4 or greater than about 5 or less than about 12 or less than about 10 or less than about 9 or less than about 8 or less than about 7 or combinations thereof. In an embodiment, "d" may be less than 1 or less than 0.50 or less than 0.40. In an embodiment, "f" may be less than about 50. The process may further comprise adding UZM-53 seeds to the reaction mixture. Sources of M include but are not limited to sodium hydroxide, potassium hydroxide, sodium aluminate, potassium aluminate, sodium silicate, and potassium silicate. Sources of MX include sodium chloride, sodium bromide, sodium iodide, potassium chloride, potassium bromide, and potassium iodide. In an embodiment, the source of MX is selected from the group consisting of sodium chloride, potassium chloride and combinations thereof. Sources of R1 can include aqueous solutions, liquid or solid diisopropanolamine or combinations thereof. Solutions of diisopropanolamine are highly preferred. Diisopropanolamine is a low melting (approximately 40° C.) solid which is not easily handled. The IUPAC name is 1-(2-hydroxypropylamino)propan-2-ol. The material either needs to be chipped out of a container or melted and then handled as a liquid, but it readily refreezes unless it is kept at higher than room temperature. However, solutions of DIPA are stable and readily prepared by melting the material and adding water while stirring to make an aqueous solution. The concentration of the R1 solution may be about 50 wt % or may be in the range from about 10 wt % to about 90 wt % or may be in the range from 30 wt % to about 70 wt % or may be in the range from about 40 wt % to about 60 wt %. These solutions may then be easily used in the synthesis. The source of E is selected from the group consisting of alkali borates, boric acid, precipitated gallium oxyhydroxide, gallium sulfate, ferric sulfate, ferric chloride and mixtures thereof. The sources of aluminum include but are not limited to aluminum alkoxides, precipitated aluminas, aluminum metal, aluminum hydroxide, sodium aluminate, potassium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, fumed silica, precipitated silica and alkali silicates.

In an embodiment, the reaction mixture is a low flammability reaction mixture. The flashpoint of a reaction mixture can be determined by ASTM D93 Standard Test Methods for Flash Point by Pensky-Martens Closed Cup Tester. In an aspect, a low flammability reaction mixture is one with a flashpoint greater than 50° C. or greater than 60° C. or greater than 75° C. Higher values of the flashpoint by ASTM D93 indicate lower flammability. The reaction mixture is reacted at a temperature of about 150° to about 185° C. for a time of about 1 day to about 3 weeks in a stirred, sealed reaction vessel under autogenous pressure. After crystallization is complete, the solid product is isolated from the heterogeneous mixture by means such as filtration or centrifugation, and then washed with deionized water and dried in air at ambient temperature up to about 100° C. Preferably, the reaction mixture is reacted at a temperature of about 165° to about 175° C. for a time of about 1 day to about 3 weeks. In an embodiment, the reaction mixture is reacted at a temperature of about 165° to about 175° C. for a time of about 1 day to about 1 week.

UZM-53, in the as-synthesized and anhydrous basis, is characterized by the x-ray diffraction pattern, having at least the d-spacings and relative intensities set forth in Table 1 below. Those peaks characteristic of UZM-53 are shown in Table 1. Additional peaks, particularly those of very weak intensity, may also be present. All peaks of medium or higher intensity present in UZM-53 are represented in Table 1. Diffraction patterns herein were obtained using a typical laboratory powder diffractometer, utilizing the $K_\alpha$ line of copper; Cu K alpha. From the position of the diffraction peaks represented by the angle 2theta, the characteristic interplanar distances $d_{hkl}$ of the sample can be calculated using the Bragg equation. The intensity is calculated on the basis of a relative intensity scale attributing a value of 100 to the line representing the strongest peak on the X-ray diffraction pattern, and then: weak (w) means less than 15; weak to medium (w-m) means in the range 8 to 35; medium (m) means in the range 15 to 50; medium to strong (m-s) means in the range 35 to 60; strong (s) means in the range 50 to 90; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular morphological structures or for samples with crystals which are small enough to cause significant broadening of the X-rays. This can also be the case when the equipment or operating conditions used to produce the diffraction pattern differ significantly from those used in the present case.

TABLE A

| 2θ | d(Å) | I/I$_0$ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W—M |
| 19.72 | 4.50 | S |
| 20.04 | 4.43 | W—M |
| 21.00 | 4.23 | S |
| 21.50 | 4.13 | W—M |
| 22.90 | 3.88 | VS |
| 24.10 | 3.69 | VS |
| 24.62 | 3.61 | S |
| 25.34 | 3.51 | M—S |
| 26.02 | 3.42 | W |
| 28.30 | 3.15 | W—M |
| 31.62 | 2.83 | W—M |
| 35.60 | 2.52 | M—S |

In an embodiment, the peak at d=3.88 Å is the strongest peak. In an embodiment, two peaks of very strong intensity are present. In an embodiment, only two peaks of very strong intensity are present. In an embodiment, three peaks of strong intensity are present. As will be shown in detail in the examples, the UZM-53 material is thermally stable up to a temperature of at least 600° C. and in another embodiment, up to at least 800° C. Also as shown in the examples, the UZM-53 material may have a micropore volume as a percentage of total pore volume of less than 70% or less than 60% or less than 55% as determined by BET analysis using N$_2$.

As synthesized, the UZM-53 material will contain some exchangeable or charge balancing cations in its pores. These exchangeable cations can be exchanged for other cations, or in the case of organic SDAs, they can be removed by heating under controlled conditions. It may be possible to remove some organic SDAs from the UZM-53 zeolite directly by ion exchange. The UZM-53 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination and on an anhydrous basis, the microporous crystalline zeolite UZM-53 has a three-dimensional framework of at least AlO$_2$ and SiO$_2$ tetrahedral units and an empirical composition in the hydrogen form expressed by an empirical formula of where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 1, "N" is the weighted average valence of M1 and has a value of about +1 to about +3, E is an element selected from the group consisting of gallium, iron, boron, and combinations thereof, x' is the mole fraction of E and varies from 0 to 1.0, y' is the mole ratio of Si to (Al+E) and varies from greater than about 12 to about 30 and z" is the mole ratio of O to (Al+E) and has a value determined by the equation:

$$z"=(a \cdot N+3+4 \cdot y')/2.$$

In an embodiment, "a" may vary from about 0.05 to about 0.75 or may vary from about 0.1 to about 0.5. In an embodiment, "y" may be greater than 12 or greater than 15 or greater than 17 or less than 25 or less than about 22 or less than about 20. In an embodiment, when M1 comprises a combination of sodium and potassium cations, the molar ratio of $Na^+/K^+$ in $M1^+$ is in the range 0.10 to 2, and is preferably in the range of about 0.2 to about 0.9. The molar ratio of $Na^+/K^+$ may be in the range from about 0.2 to about 0.75. In the calcined form, UZM-53 displays the XRD pattern shown in Table B. Those peaks characteristic of UZM-53 are shown in Table B. Additional peaks, particularly those of very weak intensity, may also be present. All peaks of medium or higher intensity present in UZM-53 are represented in Table B.

TABLE B

| 2θ | d(Å) | I/I₀ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W |
| 19.72 | 4.50 | VS |
| 20.04 | 4.43 | W—M |
| 21.00 | 4.23 | S |
| 21.50 | 4.13 | W |
| 22.90 | 3.88 | S |
| 24.10 | 3.69 | S |
| 24.62 | 3.61 | M |
| 25.34 | 3.51 | M |
| 26.02 | 3.42 | M |
| 28.30 | 3.15 | W—M |
| 31.62 | 2.83 | W—M |
| 35.60 | 2.52 | M |

The intensity is calculated on the basis of a relative intensity scale attributing a value of 100 to the line representing the strongest peak on the X-ray diffraction pattern, and relative intensities are described above. In an embodiment, the peak at d=4.5 Å is the strongest peak. In an embodiment, only one peak of very strong intensity is present. In an embodiment, 3 peaks of strong intensity are present.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-53 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species. The separation process may comprise contacting at least two components with the UZM-53 zeolite material to generate at least one separated component.

The UZM-53 zeolite of this invention can also be used as a catalyst or catalyst support in various hydrocarbon conversion processes. The catalyst may contain from about 0 wt % or about 10 wt % to about 80 wt % or about 100 wt % of the UZM-53 zeolite. Hydrocarbon conversion processes are well known in the art and include oligomerization, hydrocracking, hydroisomerization, hydrotreating, hydrodenitrogenation, hydrodesulfurization, naphthene ring opening, paraffin isomerization, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

Using a UZM-53 catalyst composition which contains a hydrogenation promoter such as platinum or palladium, heavy petroleum residual stocks, cyclic stocks and other hydrocrackable charge stocks can be hydrocracked at temperatures in the range of about 204° C. to about 649° C. (400° to 1200° F.) or about 316° C. to about 510° C. (600° F. and 950° F.). Nickel, cobalt, molybdenum and tungsten are additionally known in the art as hydrogenation promoters. Reaction pressures are in the range of atmospheric to about 24,132 kPa g (3,500 psig), or between about 1379 to about 20,685 kPa g (200 to 3000 psig). Contact times usually correspond to liquid hourly space velocities (LHSV) in the range of about 0.1 $hr^{-1}$ to 15 $hr^{-1}$, preferably between about 0.2 and 10 $hr^{-1}$. Hydrogen circulation rates are in the range of 178 to about 8,888 std. $m^3/m^3$ (1,000 to 50,000 standard cubic feet (scf) per barrel of charge), or about 355 to about 5,333 std. $m^3/m^3$ (about 2,000 to about 30,000 scf per barrel of charge). Suitable hydrotreating conditions are generally within the broad ranges of hydrocracking conditions set out above.

These same catalysts, i.e. those containing hydrogenation promoters, are also useful in hydroisomerization processes in which feedstocks such as normal paraffins are converted to saturated branched chain isomers. Hydroisomerization is carried out at a temperature of from about 93° C. to about 450° C. (200° F. to 842° F.), preferably about 150° C. to about 300° C. (300° F. to 572° F.) with an LHSV value of from about 0.2 to 1.0. Hydrogen is supplied to the reactor in admixture with the hydrocarbon feedstock in molar proportions ($H_2$/HC) of between 1 and 5.

Catalytic cracking processes are preferably carried out with the UZM-53 composition using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Alkylation of aromatics usually involves reacting an aromatic ($C_2$ to $C_{12}$), especially benzene, with a monoolefin to produce a linear alkyl substituted aromatic. The process is carried out at an aromatic: olefin (e.g., benzene:olefin) ratio of between 1:1 and 30:1, a olefin LHSV of about 0.3 to about 10 $hr^{-1}$, a temperature of about 100° to about 250° C. and pressures of about 1379 kPa g to about 6895 kPa g (about 200 to about 1000 psig). Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,895 kPa (1,000 psig) and a weight hourly space velocity (WHSV) of 0.1 to about 120. Details on paraffin alkylation may be found in U.S. Pat. Nos. 5,157,196 and 5,157,197, which are incorporated by reference.

Isomerization reactions are carried out under conditions identified for the feedstock. Olefins are preferably isomerized at temperatures of about 150° C. to about 500° C. (302° F.-932° F.), while paraffins, naphthenes and alkyl aromatics are isomerized at temperatures of from about 350° C. to about 550° C. (662° F.-1022° F.). Particularly desirable isomerization reactions contemplated herein include the conversion of n-heptane and/or n-octane to isoheptanes, iso-octanes, butane and iso-butane, methylcyclopentane to cyclohexane, meta-xylene and/or ortho-xylene to paraxylene, 1-butene to 2-butene and/or isobutene, n-hexene to iso-hexene, cyclohexene to methylcyclopentene etc.

Catalyst compositions comprising UZM-53 may be particularly useful for the oligomerization of olefins to longer olefins such as gasoline and distillate range olefins. Light olefins such as ethene, propene, butene and pentenes may be oligomerized to gasoline or distillate range olefins. Liquid phase operation is typically preferred. Operating pressures may include between about 2.1 MPa (300 psia) and about 10.5 MPa (1520 psia), but other pressures are contemplated depending on feed and recycle such that liquid phase is maintained. With liquid oligomerate recycle, lower pressures are often possible to maintain liquid phase. Temperature may be in a range between about 100° C. and about 350° C. or may be between about 180° C. and about 300° C. The weight hourly space velocity may be between about 0.5 and about 10 hr$^{-1}$. Additional conditions for successful operation may be given in U.S. Pat. No. 9,278,893, hereby incorporated by reference.

The proton (W) form of UZM-53 may additionally be characterized by infrared spectroscopy coupled with probe molecules. Ammonia is capable of accessing all acid sites in a MTT zeolite comprising 10-membered ring pores. Adsorbed $NH_3$ coordinates with both Brönsted and Lewis acid sites. A distinct infrared absorbance band is observed for both types of acid sites. The integrated band area gives a relative measure of total number of acid sites. Discrete desorption experiments provide a relative measure of acid site strength. UZM-53 possesses only small amounts of Lewis acid sites. In an embodiment, the $NH_3$ Lewis acid value may be less than 0.05 or may be less than 0.04 or may be less than 0.03. UZM-53 possesses large quantities of Brønsted acid sites. In an embodiment, the $NH_3$ Brønsted value may be greater than 3.00 or may be greater than 4.00 or may be greater than 4.50 or may be greater than 5.00. Collidine adsorption experiments performed in analogous manner yield equivalent information on the external Brönsted acidity of catalyst materials. Collidine (2,4,6-trimethylpyridine) is too large to enter the 10-membered ring of MTT zeolites. UZM-53 possesses only small amounts of external Bronsted acidity. In an embodiment, the Collidine Brønsted value may be less than 0.12 or may be less than 0.10.

The invention will now be further illustrated by the following non-limiting examples.

Example 1

Of sodium hydroxide (99% purity), 0.675 g were weighed into a 250 cc Teflon beaker and 1.085 g potassium hydroxide (87.3% purity) was added. Then, 55.9 g water and a stir bar were added and stirring started. When this became a clear solution, 2.43 g aluminum hydroxide (27.9% Al by analysis) was added. When this became a clear solution 42.69 g of a 50% aqueous solution of diisopropanolamine was added. Next, 4.14 g tetramethyl-1,3propanediamine (99+% purity) was added. Finally, 75 g LudoxAS-40 was slowly added. This became a thin, pourable gel. The gel was transferred to a 300 cc stirred autoclave and digested at 175° for 120 hours at 250 rpm.

Figure 1:
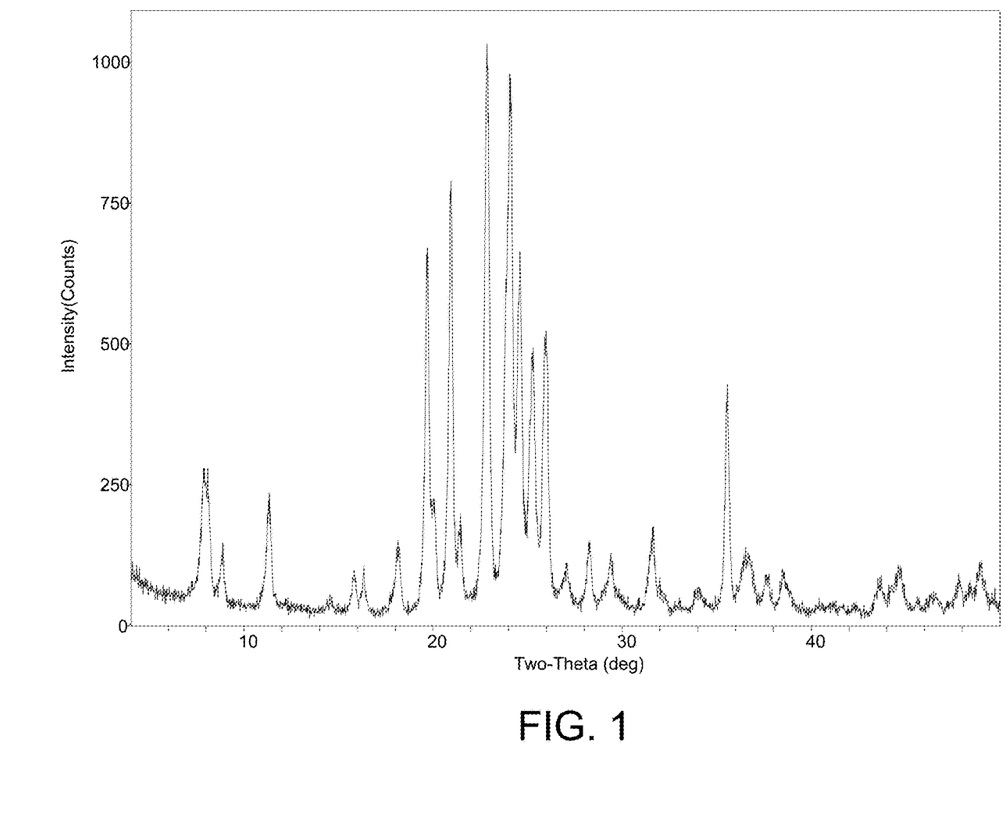
FIG. 1 is an XRD pattern of the UZM-53 zeolite formed in Example 1. This pattern shows the UZM-53 zeolite in the as-synthesized form.
Figure 2:
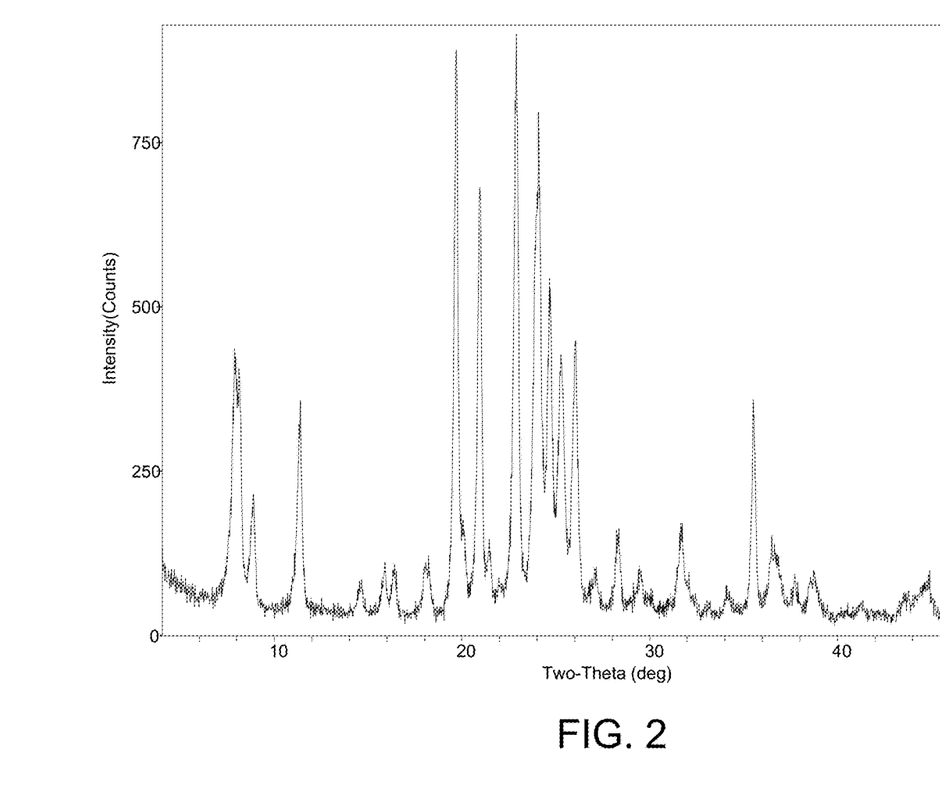
FIG. 2 is also an XRD pattern of the UZM-53 zeolite formed in Example 1. This pattern shows the UZM-53 zeolite after calcination.

The solid product was recovered by filtration, washed with de-ionized water and dried at 95° C. The resulting product was identified to be UZM-53 by XRD and is shown in FIG. 1. The composition of the product consisted of the following mole ratios: Si/Al=18.14, Na/Al=0.105, K/Al=0.195, N/Al=1.125, and C/N=3.75. This material was then calcined under air at 600° for 12 hours. Surface area analysis showed a BET SA of 178 m$^2$/g, total pore volume of 0.166 mL/g and a micropore volume of 0.081 mL/g. The XRD of the calcined material is shown in FIG. 2. A portion was then ion-exchanged four times with ammonium nitrate at 75° C. for an hour each time before activation at 500° C. for 2 hours in air to yield the H$^+$ form. In FIGS. 1 and 2, Two-Theta (deg) is on the x-axis and Intensity (Counts) on the y-axis.

Example 2

Of sodium hydroxide (99% purity), 0.44 g were weighed into a 250 cc Teflon beaker and 0.74 g potassium hydroxide (87.3% purity) was added. Then, 51.5 g water and a stir bar were added and stirring started. When this became a clear solution, 1.62 g aluminum hydroxide (27.9% Al by analysis) was added. When this became a clear solution 14.28 g diisopropanolamine (98% purity) was added. Next, 2.76 g tetramethyl-1,3propanediamine (99+% purity) was added. Finally, 50 g LudoxAS-40 was slowly added. This became a thin, pourable gel. The reaction mixture with Si/Al=20 was transferred equally to 4 45 mL autoclaves and digested at 175° while tumbling at 15 rpm in a rotisserie oven for 4, 5, 6, and 7 days, respectively.

The solid products were recovered by filtration, washed with de-ionized water and dried at 95° C. The product resulting from all reactions were identified to be UZM-53 by XRD, with the 4 day material still containing some amorphous product. The composition of the product from the 5 day synthesis consisted of the following mole ratios: Si/Al=19.34, Na/Al=0.064, K/Al=0.17, N/Al=1.31, and C/N=3.60. This material was then calcined under air at 600° for 18 hours. Surface area analysis showed a BET surface area of 178 m$^2$/g, total pore volume of 0.157 mL/g and a micropore volume of 0.084 mL/g.

Comparative Example 3

Of sodium hydroxide (99% purity), 0.47 g were weighed into a 250 cc Teflon beaker and 0.71 g potassium hydroxide (87.3% purity) was added. Then, 51.5 g water and a stir bar were added and stirring started. When this became a clear solution, 1.08 g aluminum hydroxide (27.9% Al by analysis) was added. When this became a clear solution 14.35 g diisopropanolamine (98% purity) was added. Finally, 50 g LudoxAS-40 was slowly added. This became a thin, pourable gel. The reaction mixture of Si/Al=30.5 was transferred equally to 4 45 mL autoclaves and digested at 175° while tumbling at 15 rpm in a rotisserie oven for 4, 5, 6, and 7 days, respectively.

Figure 3:
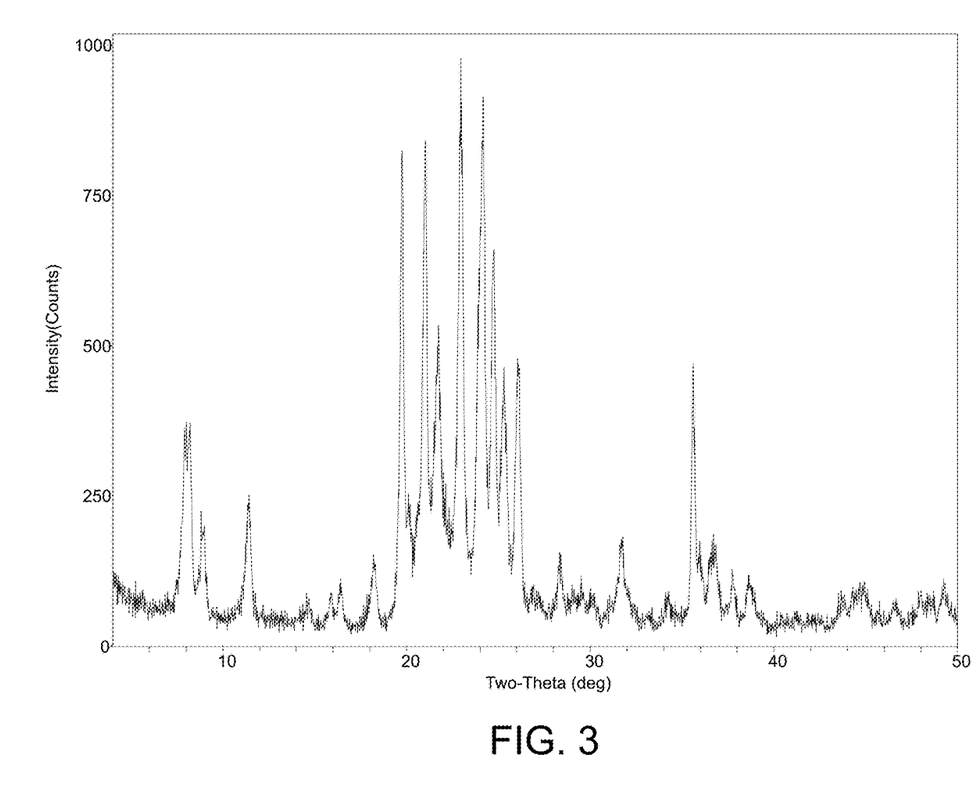
FIG. 3 is an XRD pattern of the MTT zeolite formed in Comparative Example 3. This pattern shows the MTT zeolite after calcination.

The solid products were recovered by filtration, washed with de-ionized water and dried at 95° C. The product resulting from all reactions were identified to be MTT by XRD, with the 5 and 6 day materials containing some cristobalite. At 76 hours, this same reaction mixture had been amorphous in a previous experiment. The composition of the product from the 4 day synthesis consisted of the following mole ratios: Si/Al=26.8, Na/Al=0.13, K/Al=0.37, N/Al=0.76, and C/N=5.63. The XRD of the material is shown in FIG. 3. Two peaks of very strong intensity and 4 peaks of strong intensity are present.

Comparative Example 4

Of sodium hydroxide (99% purity), 0.48 g were weighed into a 250 cc Teflon beaker and 0.71 g potassium hydroxide (87.3% purity) was added. Then, 51.5 g water and a stir bar were added and stirring started. When this became a clear solution, 1.24 g aluminum hydroxide (27.9% Al by analysis) was added. When this became a clear solution 14.23 g diisopropanolamine (98% purity) was added. Finally, 50 g LudoxAS-40 was slowly added. This became a thin, pourable gel. The reaction mixture of Si/Al=26 was transferred equally to 4 45 mL autoclaves and digested at 175° while tumbling at 15 rpm in a rotisserie oven for 4, 5, 6, and 7 days, respectively. The solid products were recovered by filtration, washed with de-ionized water and dried at 95° C. The product resulting from all reactions were largely amorphous by XRD.

Example 5

Of sodium hydroxide (99% purity), 0.48 g were weighed into a 250 cc Teflon beaker and 0.73 g potassium hydroxide (87.3% purity) was added. Then, 51.5 g water and a stir bar were added and stirring started. When this became a clear solution, 1.62 g aluminum hydroxide (27.9% Al by analysis) was added. When this became a clear solution, 14.39 g diisopropanolamine (98% purity) was added. Next, 1.38 g tetramethyl-1,3propanediamine (99+% purity) was added. Finally, 50 g LudoxAS-40 was slowly added. This became a thin, pourable gel. A portion of the gel was analyzed for flammability and found to have a 80° C. flashpoint. The remaining gel was transferred equally to 5 45 mL autoclaves and 4 digested at 175° while tumbling at 15 rpm in a rotisserie oven for 5, 6, 7, and 8 days, respectively, while 1 was heated statically at 175° C. for 6 days.

The solid products were recovered by filtration, washed with de-ionized water and dried at 95° C. The product resulting from the reaction was identified to be UZM-53 by XRD. The composition of the product from the 5 day synthesis consisted of the following mole ratios: Si/Al=19.4, Na/Al=0.11, K/Al=0.23, N/Al=1.13, and C/N=3.92.

Example 6

Liquid sodium aluminate and liquid potassium aluminate were combined while stirring. Diisopropanolamine was then added. Next, tetramethyl-1,3propanediamine (99+% purity) was added. Finally, LudoxAS-40 was slowly added. This became a thin, pourable gel of composition 1 $Al_2O_3$:40 $SiO_2$:0.68 $Na_2O$:0.66 $K_2O$:12.5 DIPA:2.53 TMPDA:542 $H_2O$. The gel was transferred to a 2 L autoclave and digested at 175° while stirring at 300 rpm for 144 hours.

Figure 4:
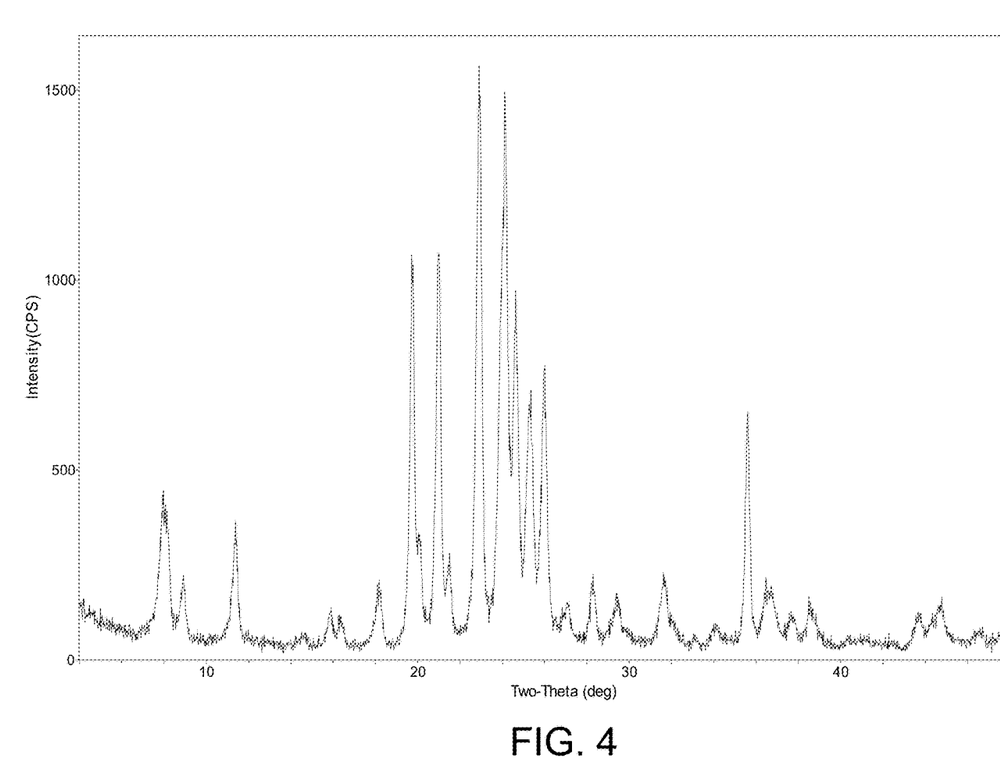
FIG. 4 shows the UZM-53 product formed in Example 6. This pattern shows the UZM-53 zeolite in the as-synthesized form.
Figure 5:
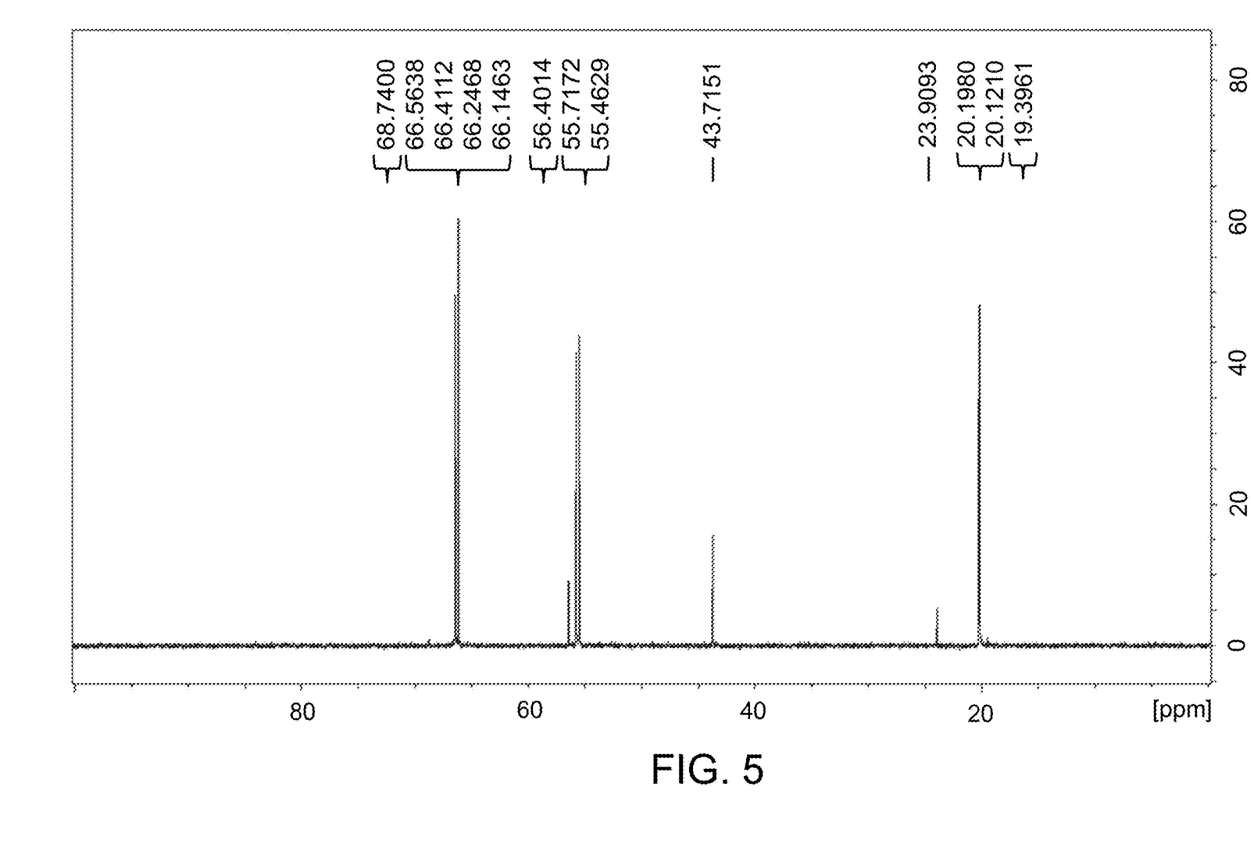
FIG. 5 shows the $^{13}C$ NMR spectrum obtained of the mother liquor from Example 6 showing the presence of two organic structure directing agents.

The solid products were recovered by filtration, washed with de-ionized water and dried at 95° C. The product resulting from the reaction was identified to be UZM-53 by XRD and is shown in FIG. 4. A portion of the mother liquor from the filtration was saved before washing and analyzed by $^{13}C$ NMR, which is shown in FIG. 5. Six peaks of approximately equivalent intensity were observed for diisopropanolamine and three peaks in a 1:4:2 ratio were observed for tetramethylpropanediamine. The molar ratio of diisopropanolamine to tetramethylpropanediamine was about 11.5.

| Peak Location (ppm) | Integral |
|---|---|
| 20.12 | 15.2 |
| 20.20 | 15.2 |
| 23.91 | 1.2 |
| 43.72 | 5.3 |
| 55.46 | 14.7 |
| 55.72 | 15.2 |
| 56.40 | 2.7 |
| 66.15 | 14.9 |
| 66.41 | 15.2 |

Figure 6:
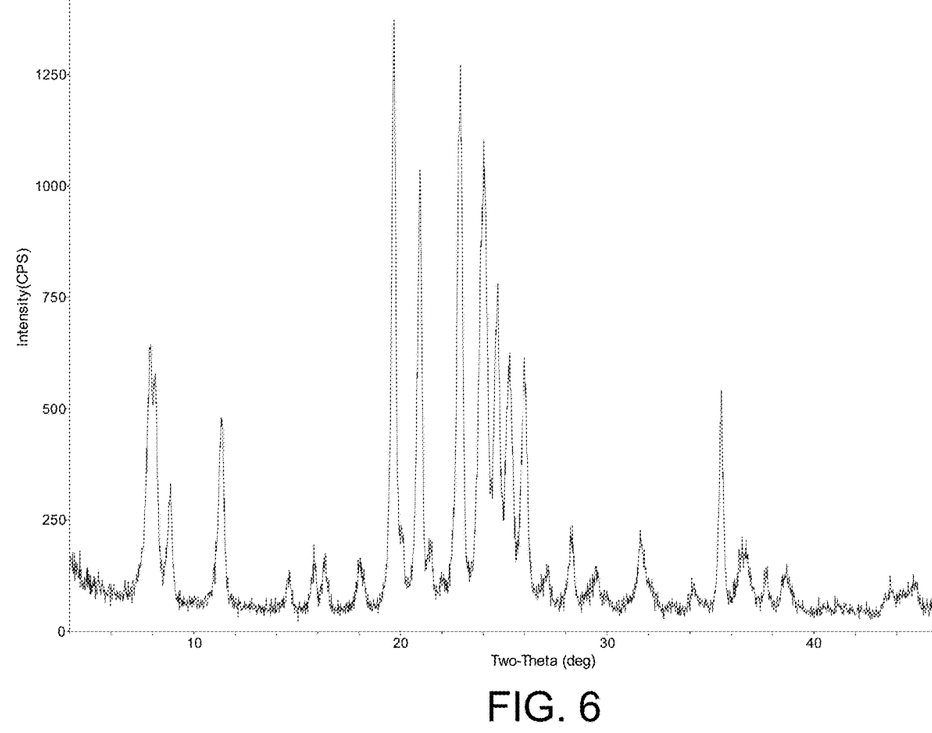
FIG. 6 shows the XRD pattern of the UZM-53 zeolite of Example 6 in the calcined form.
Figure 7:
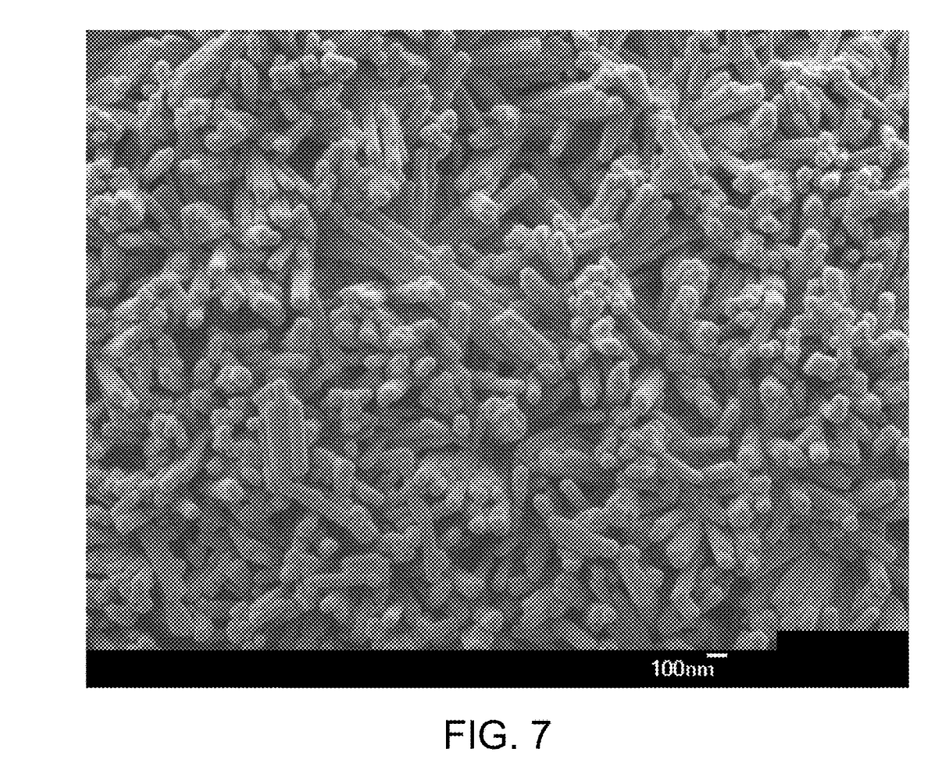
FIG. 7 shows a SEM photo of the Example 6 UZM-53 product at 100 nm resolution.
Figure 8:
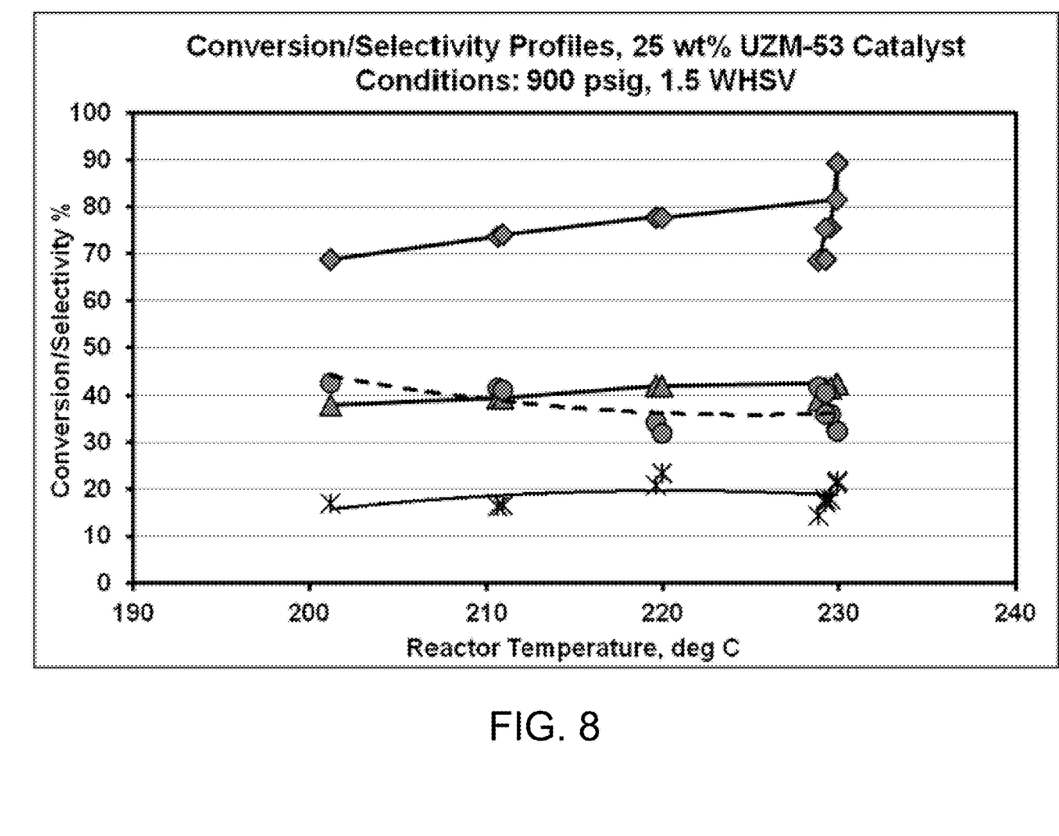
FIG. 8 shows hydrocarbon conversion in the form of olefin oligomerization from use of the UZM-53 zeolite catalyst as described in Example 11.

Another portion of the mother liquor was analyzed for flash point and found to have a flash point of >90° C. The composition of the product consisted of the following mole ratios: Si/Al=18.9, Na/Al=0.069, K/Al=0.18, N/Al=1.26, and C/N=3.77. This material was then calcined under air at 600° C. for 12 hours. The XRD pattern of the calcined UZM-53 is shown in FIG. 6. The product was then ion-exchanged three times with $NH_4NO_3$ and calcined at 550° C. for 3 hours to yield the ft form. An SEM photo at 100 nm range is shown in FIG. 7.

Example 7

Liquid sodium aluminate and liquid potassium aluminate were combined while stirring. Sodium chloride and potassium chloride were then added. Diisopropanolamine was then added. Next, tetramethyl-1,3propanediamine (99+% purity) was added. Finally, LudoxAS-40 was slowly added. This became a thin, pourable gel of composition 1 $Al_2O_3$:40 $SiO_2$:0.68 $Na_2O$:2.96 NaCl:2.96 KCl:0.66 $K_2O$:12.5 DIPA: 0.32TMPDA:543 $H_2O$. Of the gel, 831 g was transferred to a 2 L autoclave and digested at 175° C. while stirring at 300 rpm for 119 hours. The solid products were recovered by filtration, washed with de-ionized water and dried at 95° C. 157 g product were recovered. The product resulting from the reaction was identified to be UZM-53 by XRD. The composition of the product consisted of the following mole ratios: Si/Al=19.4, Na/Al=0.07, K/Al=0.53, N/Al=0.59, and C/N=5.04.

Example 8

In the present invention, the presence of Brönsted and Lewis acid sites were determined by infrared spectroscopy using the following standard procedures. All procedures started with sample preparation and activation. The samples were ground and pressed into self-supporting pellets. Pre-treatment of samples was performed in-situ in UHP 20% $O_2/N_2$ gas flow at 500° C. for 2 hours to remove water. Gas flow was switched to He and the sample was cooled to room temperature and the hydroxyl spectrum was recorded.

Total acidity determination: The sample was heated to 150° C. and once at this temperature; 1% $NH_3$ in UHP He was flowed over the sample for 10 minutes followed by equilibration of the sample for an additional 50 minutes. Samples were cooled to room temperature and excess $NH_3$ was purged in He flow. Desorption experiments were performed by heating the sample in He flow to 150° C. holding at temperature for 1 hour then cooling to room temperature and recording a spectrum. The pretreated spectrum was subtracted from each desorption spectra and the Brönsted and/or Lewis acid site adsorbed absorbance bands integrated to determine the relative total acidity of the materials. The value of the Lewis acid peak divided by the sample mass gives the $NH_3$ Lewis acid value (area/mg). The value of the Brønsted peak divided by the sample mass gives the $NH_3$ Brønsted acid value (area/mg).

The external Brönsted acidity determination: The sample is heated to 150° C. and once at temperature He saturated with collidine at 7° C. is flowed over the sample for 10 minutes followed by equilibration of the sample for an additional 50 minutes. Sample is cooled to room temperature and excess collidine is purged with He flow. Desorption experiments are performed by heating the sample in He flow to 150° C. holding at temperature for 1 hour then cooling to room temperature and recording a spectrum. The pretreated spectrum was subtracted from the desorption spectra and Brönsted acid site adsorbed absorbance bands were integrated to determine the Collidine Brønsted value per milligram of the materials (area/mg).

In addition to materials described in the examples, a sample of MTT zeolite from Zeolyst was purchased which had Si/Al=23. All materials were tested in H+ form.

Table of Data

| Sample | Collidine Brønsted | $NH_3$ Lewis | $NH_3$ Brønsted |
|---|---|---|---|
| Zeolyst MTT | 0.25 | 0.021 | 4.98 |
| Example 6 | 0.12 | 0.04 | 5.33 |
| COMP Example 9 | 0.22 | 0.052 | 2.42 |
| Example 1 | 0.10 | 0.027 | 4.88 |
| Repeat Example 1 | 0.10 | 0.031 | 4.99 |

Comparative Example 9

Example 1 of U.S. Pat. No. 4,076,842 was repeated. Twice the amount of reaction mixture was created to allow analysis for flammability. The reaction mixture had a flashpoint of 49.5° C. The solid products were recovered by filtration, washed with de-ionized water and dried at 95° C. The product resulting from the reaction after 4 or 6 days was identified to be ZSM-23 by XRD.

Comparative Example 10

Isobutylamine was utilized as the organic structure directing agent for preparation of a MTT zeolite from a mixture of composition 45 $SiO_2$:Al:5.50 NaOH:9 $iBuNH_2$:834 $H_2O$ Weighed 223.88 g deionized water into a large beaker and, with overhead stirring added 4.73 g NaOH pellets. Clear solution in ~5 min. Added 123.89 g Ludox AS40 while mixing. Now an opaque solution. Added 33.34 g of Nalco 1056 (1.74% Al, 12.0% Si, 0.026% Na). Mixed for 15 min after the addition of the Nalco sol. Still a thin white solution. Added 14.15 g isobutylamine (99% Aldrich) dropwise, stirred 5-7 minutes. Thin translucent white liquid, pH=12.80 A portion of this liquid was analyzed for flammability and determined to have a flashpoint of 35° C. The remaining gel was then split into 2 and ~197 g loaded into separate 300 cc reactors. Both stirred autoclaves were ramped to 150° C. in 8 h. Reactor A was held at 150° C. for 48 h, while Reactor B was held at 150° C. for 120 h. An anchor-type stirrer was used with a setting of 250 rpm. After 2 days, reactor A was worked up. The product was a mixture of thin, white liquid and thick, white paste with pH=10.71. The product was centrifuged at 10,000RPM and washed with water then dried at 100° C. Yield: 25.68 g. Analytical results showed 2.88 wt % C, 0.84 wt % N, 45.2 wt % Si, 1.07 wt % Al and 1 wt % Na.

Example 11

The calcined form of the Example 6 UZM-53 material was ion-exchanged to the H+ form and then extruded as ⅛" cylinders in a 25% UZM-53/75% $Al_2O_3$ formulation, dried at 110° C. overnight and then calcined to 550° C. to give the UZM-53/$Al_2O_3$ catalyst. The feed for the oligomerization experiment was as shown in Table 1. The oligomerization feed was contacted with the UZM-53 catalyst at 900 psig, 1.5 WHSV at a range of weight average bed temperatures from 200-230° C. after a break-in period of 75 hours at 0.75 and 1.5 WHSV to yield the results shown in Table 2 and FIG. 6. The UZM-53 catalyst is active and selective in converting light olefins to distillate range product. In FIG. 6, total C4 olefin conversion in weight percent is indicated in gray diamonds with black outline, selectivity to C8-C11 compounds in gray circles with black outline and dashed trend line, selectivity to C12-C15 compounds in gray triangles with black outlines and selectivity to C16+ compounds in black Greek crosses.

TABLE 1

| Component | wt % |
|---|---|
| C3 | 0.037 |
| C3= | 0.172 |
| iC4 | 69.276 |
| nC4 | 0.093 |
| iC4= | 7.854 |
| 1-C4= | 5.885 |
| 2-C4= | 16.516 |
| C5= | 0.167 |

TABLE 2

| HOS | WABT | C4 = conversion | nC4 = conversion | iC4 = conversion | C5-C7 selectivity | C8-C11 selectivity | C12-C15 selectivity | C16+ selectivity |
|---|---|---|---|---|---|---|---|---|
| 76 | 201 | 68.67 | 68.95 | 64.51 | 2.12 | 42.72 | 38.11 | 17.05 |
| 90 | 211 | 73.68 | 73.73 | 70.70 | 2.40 | 41.62 | 39.61 | 16.37 |
| 91 | 211 | 74.04 | 74.05 | 71.21 | 2.44 | 41.32 | 39.56 | 16.67 |
| 111 | 220 | 77.88 | 77.69 | 76.02 | 2.44 | 34.46 | 42.11 | 20.99 |
| 112 | 220 | 77.84 | 77.64 | 75.97 | 2.31 | 32.00 | 42.16 | 23.53 |
| 150 | 230 | 81.60 | 81.26 | 80.55 | 3.18 | 32.79 | 42.67 | 21.36 |
| 151 | 230 | 89.46 | 92.29 | 80.47 | 3.16 | 32.49 | 42.62 | 21.73 |
| 194 | 230 | 75.65 | 76.24 | 73.95 | 4.24 | 36.03 | 41.74 | 17.99 |

TABLE 2-continued

| HOS | WABT | C4= conversion | nC4= conversion | iC4= conversion | C5-C7 selectivity | C8-C11 selectivity | C12-C15 selectivity | C16+ selectivity |
|---|---|---|---|---|---|---|---|---|
| 195 | 229 | 75.39 | 75.97 | 73.71 | 4.20 | 36.19 | 41.62 | 18.00 |
| 270 | 229 | 68.51 | 69.34 | 66.15 | 4.49 | 42.02 | 39.09 | 14.41 |
| 271 | 229 | 68.74 | 69.55 | 66.43 | 4.53 | 40.68 | 37.61 | 17.17 |

The invention claimed is:

1. A hydrocarbon conversion process comprising contacting a hydrocarbon stream with a catalyst at hydrocarbon conversion conditions to give a converted product, the catalyst comprising a microporous crystalline zeolite having a three-dimensional framework of at least AlO$_2$ and SiO$_2$ tetrahedral units and an empirical composition in an as synthesized and anhydrous basis expressed by an empirical formula of:

$$M^+{}_m R_r Al_{1-x} E_x Si_y O_z$$

where M represents sodium, potassium or a combination of sodium and potassium exchangeable cations, "m" is the mole ratio of M to (Al+E) and varies from about 0.05 to about 1, R is the organic structure directing agent or agents derived from reactants R1 and R2 where R1 is diisopropanolamine and R2 is a chelating diamine, "r" is the mole ratio of N from the organic structure directing agent or agents to (Al+E) and has a value of from about 0.4 to about 1.5, E is an element selected from the group consisting of gallium, iron, boron and mixtures thereof, "x" is the mole fraction of E and has a value from 0 to about 1.0, "y" is the mole ratio of Si to (Al+E) and varies from greater than 12 to about 30 and "z" is the mole ratio of O to (Al+E) and has a value determined by the equation: $z=(m+3+4 \cdot y)/2$ and is characterized in that it has the x-ray diffraction pattern having at least the d-spacing's and intensities set forth in Table A:

TABLE A

| 2θ | d(Å) | I/I$_0$ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W—M |
| 19.72 | 4.50 | S |
| 20.04 | 4.43 | W—M |
| 21.00 | 4.23 | S |
| 21.50 | 4.13 | W—M |
| 22.90 | 3.88 | VS |
| 24.10 | 3.69 | VS |
| 24.62 | 3.61 | S |
| 25.34 | 3.51 | M—S |
| 26.02 | 3.42 | W |
| 28.30 | 3.15 | W—M |
| 31.62 | 2.83 | W—M |
| 35.60 | 2.52 | M—S; | wherein the hydrocarbon conversion process is selected from the group consisting of hydrocracking, hydrotreating, hydrodenitrogenation, hydrodesulfurization, naphthene ring opening, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

2. The process of claim 1 wherein said microporous crystalline zeolite has a y in said empirical formula that is less than 25.

3. The process of claim 1 wherein said microporous crystalline zeolite has a y in said empirical formula that is less than 22.

4. A hydrocarbon conversion process comprising contacting a hydrocarbon stream with a catalyst at hydrocarbon conversion conditions to give a converted product, the catalyst comprising a microporous crystalline zeolite having a three-dimensional framework of at least AlO$_2$ and SiO$_2$ tetrahedral units and an empirical composition in the hydrogen form expressed by an empirical formula of $$M1_{a'}^{N+} Al_{(1-x')} E_{x'} Si_{y'} O_{z''}$$

where M1 is at least one exchangeable cation selected from the group consisting of alkali, alkaline earth metals, rare earth metals, ammonium ion, hydrogen ion and combinations thereof, "a'" is the mole ratio of M1 to (Al+E) and varies from about 0.05 to about 1, "N" is the weighted average valence of M1 and has a value of about +1 to about +3, E is an element selected from the group consisting of gallium, iron, boron, and combinations thereof, x' is the mole fraction of E and varies from 0 to 1.0, y' is the mole ratio of Si to (Al+E) and varies from greater than about 12 to about 30 and z'' is the mole ratio of O to (Al+E) and has a value determined by the equation:

$$z''=(a \cdot N+3+4 \cdot y')/2$$

and is characterized in that it has the x-ray diffraction pattern having at least the d-spacing's and intensities set forth in Table B:

TABLE B

| 2θ | d(Å) | I/I$_0$ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W |
| 19.72 | 4.50 | VS |
| 20.04 | 4.43 | W—M |
| 21.00 | 4.23 | S |
| 21.50 | 4.13 | W |
| 22.90 | 3.88 | S |
| 24.10 | 3.69 | S |
| 24.62 | 3.61 | M |
| 25.34 | 3.51 | M |
| 26.02 | 3.42 | M |
| 28.30 | 3.15 | W—M |
| 31.62 | 2.83 | W—M |
| 35.60 | 2.52 | M; | wherein the hydrocarbon conversion process is selected from the group consisting of hydrocracking, hydrotreating, hydrodenitrogenation, hydrodesulfurization, naphthene ring opening, olefin isomerization, conversion of an aromatic molecule to another aromatic molecule, polyalkylbenzene isomerization, disproportionation of alkylbenzenes, aromatic alkylation, paraffin alkylation, paraffin cracking, naphthene cracking, reforming, hydrogenation, dehydrogenation, transalkylation, dealkylation, hydration, and dehydration.

5. The process of claim 4 wherein in the empirical formula for said microporous crystalline zeolite, y' is from about 12 to 25.

6. The process of claim 4 wherein said microporous crystalline zeolite has a $NH_3$ Lewis acid value of less than 0.05.

7. The process of claim 4 wherein said microporous crystalline zeolite has a $NH_3$ Lewis acid value of less than 0.04.

8. The process of claim 4 wherein said microporous crystalline zeolite has a $NH_3$ Lewis acid value of less than 0.03.

9. The process of claim 4 wherein said microporous crystalline zeolite has a Collidine Brønsted value of less than 0.12.

10. The process of claim 4 wherein said microporous crystalline zeolite has a Collidine Brønsted value of less than 0.1.

11. The process of claim 4 wherein said microporous crystalline zeolite has a micropore volume as a percentage of total pore volume of less than 70% as determined by BET analysis using $N_2$.

12. The process of claim 4 wherein the hydrocarbon conversion process is selected from the group of hydrocracking, hydrotreating, hydrodenitrogenation, hydrodesulfurization and combinations thereof, said catalyst further comprises a hydrogenation promoter, and said hydrocarbon conversion conditions comprise a temperature in the range of about 204° C. to about 649° C., a pressure in the range of atmospheric to about 24,132 kPa, a liquid hourly space velocity in the range of about 0.1 $hr^{-1}$ to 15 $hr^{-1}$, and a hydrogen circulation rate in the range of 178 to about 8,888 std. $m^3/m^3$.

13. The process of claim 4 wherein M1 comprises a combination of sodium and potassium cations and the molar ratio of Na/K in M1 is in the range from 0.10 to 2.

14. The process of claim 4 wherein said x-ray diffraction pattern comprises only one peak of very strong intensity.

15. A separation process comprising contacting at least two components with an adsorbent to generate at least one separated component where the separation is based either on the molecular size or on the degree of polarity of the components, the absorbent comprising a microporous crystalline zeolite having a three-dimensional framework of at least $AlO_2$ and $SiO_2$ tetrahedral units and an empirical composition in the hydrogen form expressed by an empirical formula of $$M1_{a'}^{N+}Al_{(1-x')}E_{x'}Si_{y'}O_{z''}$$

where M1 is at least one exchangeable cation selected from the group consisting of alkali, alkaline earth metals, rare earth metals, ammonium ion, hydrogen ion and combinations thereof, "a'" is the mole ratio of M1 to (Al+E) and varies from about 0.05 to about 1, "N" is the weighted average valence of M1 and has a value of about +1 to about +3, E is an element selected from the group consisting of gallium, iron, boron, and combinations thereof, x' is the mole fraction of E and varies from 0 to 1.0, y' is the mole ratio of Si to (Al+E) and varies from greater than about 12 to about 30 and z" is the mole ratio of O to (Al+E) and has a value determined by the equation:

$$z''=(a\bullet N+3+4\bullet y')/2$$

and is characterized in that it has the x-ray diffraction pattern having at least the d-spacing's and intensities set forth in Table B:

TABLE B

| 2θ | d(Å) | I/I₀ % |
|---|---|---|
| 8.02 | 11.0 | M |
| 8.92 | 9.91 | W—M |
| 11.38 | 7.77 | M |
| 15.91 | 5.56 | W |
| 16.32 | 5.43 | W |
| 18.18 | 4.88 | W |
| 19.72 | 4.50 | VS |
| 20.04 | 4.43 | W—M |
| 21.00 | 4.23 | S |
| 21.50 | 4.13 | W |
| 22.90 | 3.88 | S |
| 24.10 | 3.69 | S |
| 24.62 | 3.61 | M |
| 25.34 | 3.51 | M |
| 26.02 | 3.42 | M |
| 28.30 | 3.15 | W—M |
| 31.62 | 2.83 | W—M |
| 35.60 | 2.52 | M. |

* * * * *